US006662750B2

(12) United States Patent
Anderson et al.

(10) Patent No.: US 6,662,750 B2
(45) Date of Patent: *Dec. 16, 2003

(54) METHOD AND APPARATUS FOR CREATING A PATHWAY IN AN ANIMAL

(76) Inventors: Mark E. Anderson, 2090 Canyon Crest Ave., San Ramon, CA (US) 94583; Donald E. Anderson, 2090 Canyon Crest Ave., San Ramon, CA (US) 94583

( * ) Notice: Subject to any disclaimer, the term of this patent is extended or adjusted under 35 U.S.C. 154(b) by 0 days.

This patent is subject to a terminal disclaimer.

(21) Appl. No.: 10/304,524

(22) Filed: Nov. 26, 2002

(65) Prior Publication Data

US 2003/0188693 A1 Oct. 9, 2003

Related U.S. Application Data

(63) Continuation of application No. 10/161,575, filed on May 31, 2002, now Pat. No. 6,526,917.

(60) Provisional application No. 60/369,941, filed on Apr. 3, 2002.

(51) Int. Cl.[7] ........................ A01K 29/00; A61B 17/43

(52) U.S. Cl. ........................................ 119/174; 600/35

(58) Field of Search .............................. 119/14.21, 174, 119/860; 600/33, 34, 35; 604/510, 515, 906

(56) References Cited

U.S. PATENT DOCUMENTS

| | | | | |
|---|---|---|---|---|
| 4,403,603 A | | 9/1983 | Hutchins | 128/1 R |
| 5,360,389 A | | 11/1994 | Chenette | 600/34 |
| 5,674,178 A | | 10/1997 | Root | 600/35 |
| 6,526,917 B1 | * | 3/2003 | Anderson et al. | 119/174 |

* cited by examiner

*Primary Examiner*—Charles T. Jordan
*Assistant Examiner*—Elizabeth Shaw
(74) *Attorney, Agent, or Firm*—Kang Lim

(57) ABSTRACT

A method and apparatus for safer and more effective deep trans-cervical intra-uterine artificial insemination (AI) is provided. Such a deep AI catheter causes minimal discomfort and risk of trauma, and does not require the services of a highly trained AI professional. First, a catheter is inserted into the cervical tract of the animal. A membrane, initially positioned inside a tube section of the catheter, is then extended from an opening in the tube and into the tract under pressure. The membrane extends into the tract without friction thereby reducing the discomfort and the risk of trauma or injury to the animal. When the membrane is fully extended into the tract, pressure causes the tip of the membrane to open thereby releasing the AI fluid and depositing the genetic material suspended in the fluid into the reproductive tract. In addition to AI and embryo transplant, other applications for the pathway include other therapeutic, diagnostic or procedures, such as introducing fluoroscopic cameras, instruments, and drug delivery.

28 Claims, 14 Drawing Sheets

METHOD AND APPARATUS FOR CREATING A PATHWAY IN AN ANIMAL

PRIORITY AND INCORPORATION BY REFERENCE

This is a continuation application of U.S. patent application Ser. No. 10/161,575 filed May 31, 2002 now U.S. Pat. No. 6,526,917, titled "Method and Apparatus for creating a pathway in an animal", and claims priority from a U.S. Provisional Patent Application No. 60/369,941 entitled "Artificial Insemination Device for Swine", filed Apr. 3, 2002, which is incorporated by reference herein.

BACKGROUND OF THE INVENTION

The present invention relates to the field of creating a pathway into an animal. More particularly, the present invention relates to more effective methods and apparatus for safely creating pathways in mammals for applications such as artificial insemination (AI).

In order to feed the world population that is swelling rapidly year after year, there is an urgent need for a safer and more efficient AI of swine and other farm animals, where fresh or frozen semen and/or embryo transfer technology can be used to transfer high genetic value materials, thereby increasing the quality and quantity of the livestock litters. FIGS. 1A and 1B show conventional AI catheters for swine.

Unfortunately, freezing is usually necessitated by the short life span of fresh genetic materials and the logistics of distribution. Even with advanced freezing techniques, thawing causes a reduction in the mobility, motility and fertility of the spermatozoa, resulting in the need for trans-cervical intra-uterine AI to obtain commercially acceptable conception rates.

Referring to FIGS. 2A, 2B and 2C, a number of attempts have been made to deposit the weakened spermatozoa directly in the uterus or uterine horn by trans-cervical intra-uterine AI using rigid trans-cervical deep insemination catheters. These rigid deep insemination catheters are basically reduced diameter catheters that are enclosed and extend from within a conventional AI catheter.

The rigid deep insemination catheters are pushed and/or threaded through cervical canals using bulbous ends or slight angles on their tips in an attempt to navigate the curves and turns of the cervical canal. One inherent flaw of these rigid deep insemination catheters is their hard tips that can easily damage or puncture soft tissue areas during entry and exit procedures, often injuring or even killing the animal. Other disadvantages of these rigid catheters include the need for a professional, such as veterinarian or a highly trained technician, to perform these trans-cervical intra-uterine AI procedures, which reduces but does not substantially eliminate the risk of serious trauma and resulting sterility or death.

Hence there is a need for a safer and more effective deep trans-cervical intra-uterine AI catheter that causes minimal discomfort and risk of trauma, and does not require the services of a highly trained AI professional. Such a safer and easier-to-use AI catheter will be especially beneficial to the small farmers in third world countries who cannot afford the services of a professional.

SUMMARY OF THE INVENTION

To achieve the foregoing and in accordance with the present invention, a method and apparatus for safer and more effective deep trans-cervical intra-uterine artificial insemination (AI) is provided. Such a deep AI catheter causes minimal discomfort and risk of trauma, and does not require the services of a highly trained AI professional In one embodiment, a catheter is inserted into the cervical tract of the animal to begin creating a pathway in the reproductive tract of an animal. A membrane, initially positioned inside a tube section of the catheter, is extended from an opening in the tube and into the tract under pressure. The membrane extends into the tract without friction, i.e. without sliding action between the membrane and the tract, thereby reducing the discomfort and the risk of trauma or injury to the animal. When the membrane is fully extended into the tract, pressure causes the tip of the membrane to open thereby releasing the AI fluid and depositing the genetic material suspended in the fluid into the reproductive tract.

In addition to AI and embryo transplant, other applications for the pathway include other therapeutic, diagnostic or procedures, such as introducing fluoroscopic cameras, instruments, and drug delivery. Note that the various features of the present invention, including the extending membrane and the nozzle, can be practiced alone or in combination. These and other features of the present invention will be described in more detail below in the detailed description of the invention and in conjunction with the following figures.

BRIEF DESCRIPTION OF THE DRAWINGS

The present invention is illustrated by way of example, and not by way of limitation, in the figures of the accompanying drawings and in which like reference numerals refer to similar elements and in which.

DETAILED DESCRIPTION OF THE PREFERRED EMBODIMENTS

The present invention will now be described in detail with reference to a few preferred embodiments thereof as illustrated in the accompanying drawings. In the following description, numerous specific details are set forth in order to provide a thorough understanding of the present invention. It will be apparent, however, to one skilled in the art, that the present invention may be practiced without some or all of these specific details. In other instances, well known process steps and/or structures have not been described in detail in order to not unnecessarily obscure the present invention.

Figure 1A:
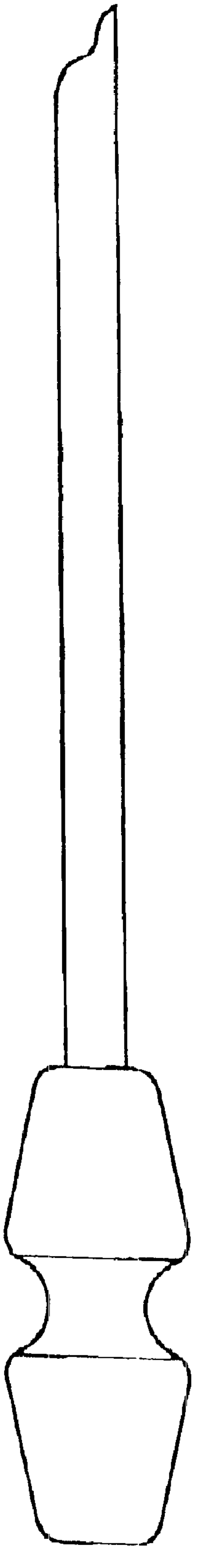
FIGS. 1A and 1B are exemplary conventional AI catheters.
Figure 1B:
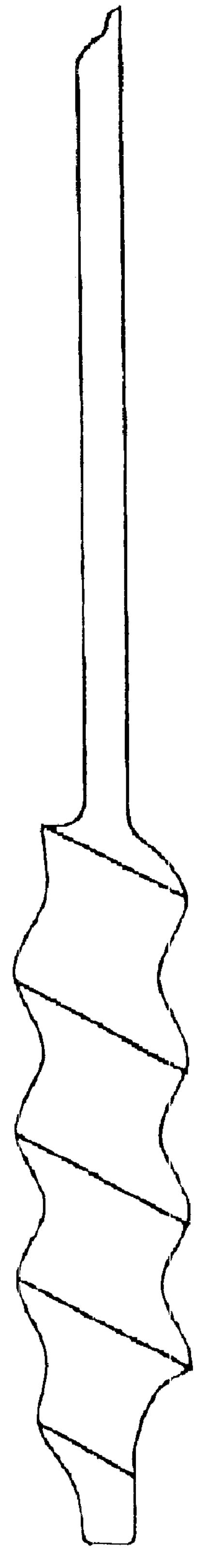
Figure 2A:
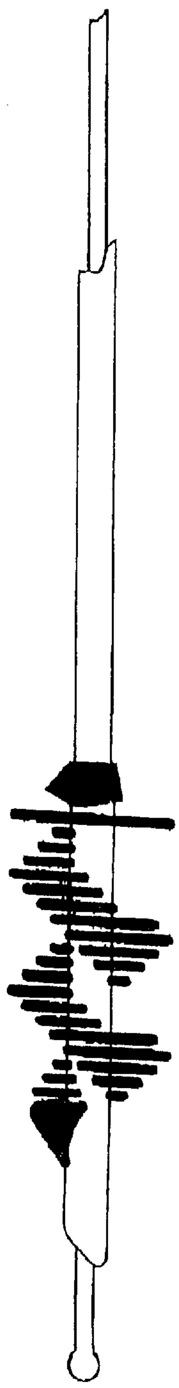
FIG. 2A, 2B and 2C show deep rigid deep insemination catheters extending from conventional AI catheters.
Figure 2B:
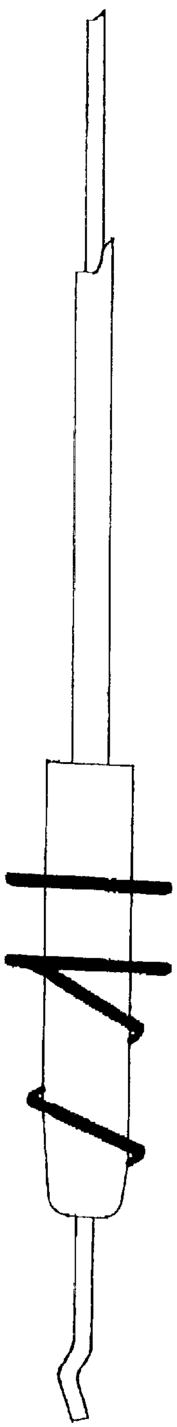
Figure 2C:
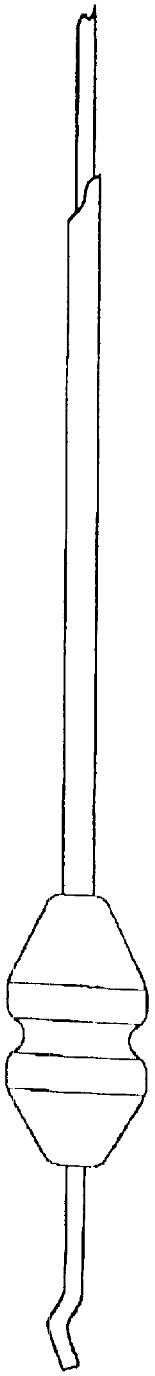
Figure 3A:
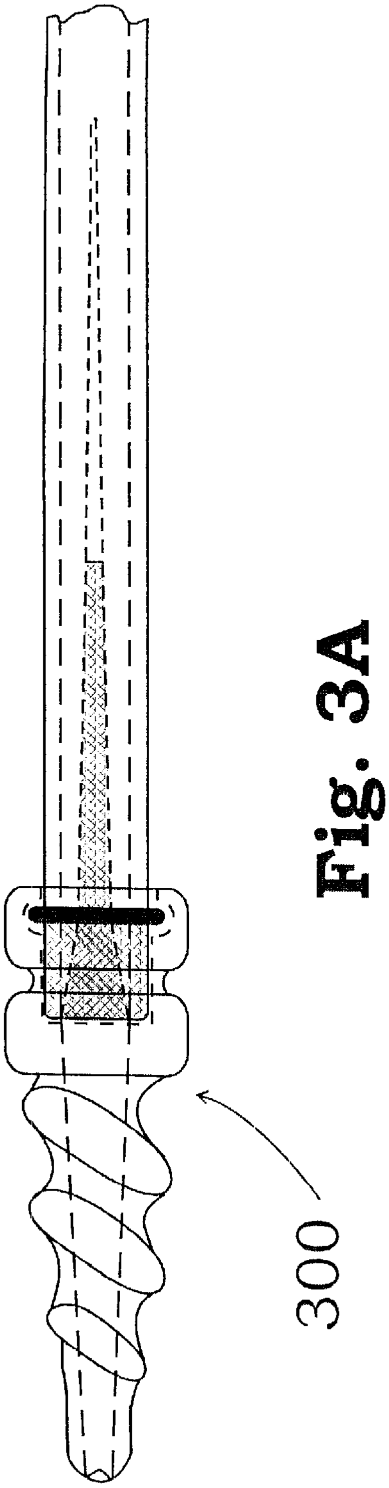
FIGS. 3A and 3B are schematic views of the before and after deployment, respectively, of one embodiment of the catheter in accordance with the present invention.
Figure 3B:
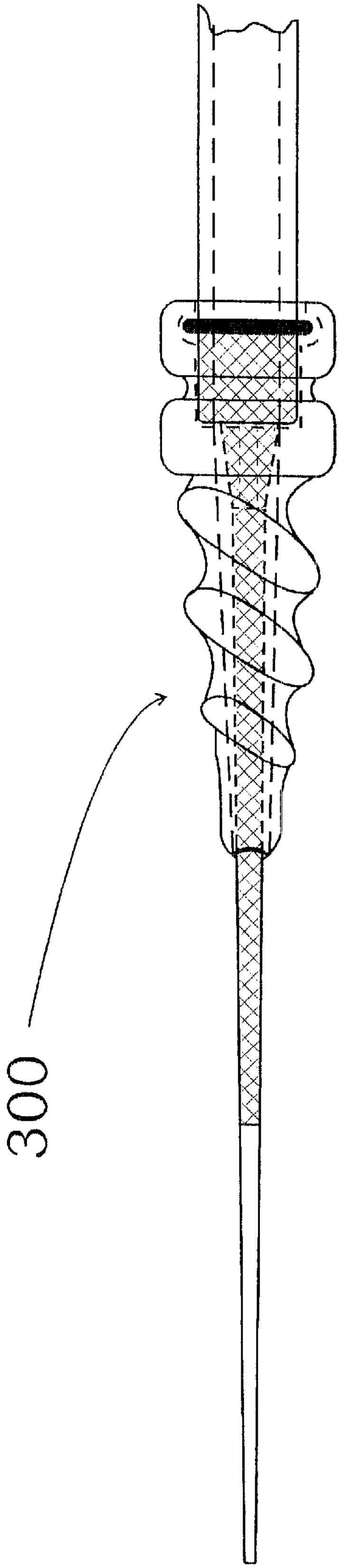

In accordance with the present invention, FIGS. 3A and 3B are views of one embodiment of catheter 300, prior to and after deployment of a membrane. FIGS. 4A through 4F illustrate the assembly of catheter 300 of FIGS. 3A and 3B.

Figures 4A, 4B, 4C:
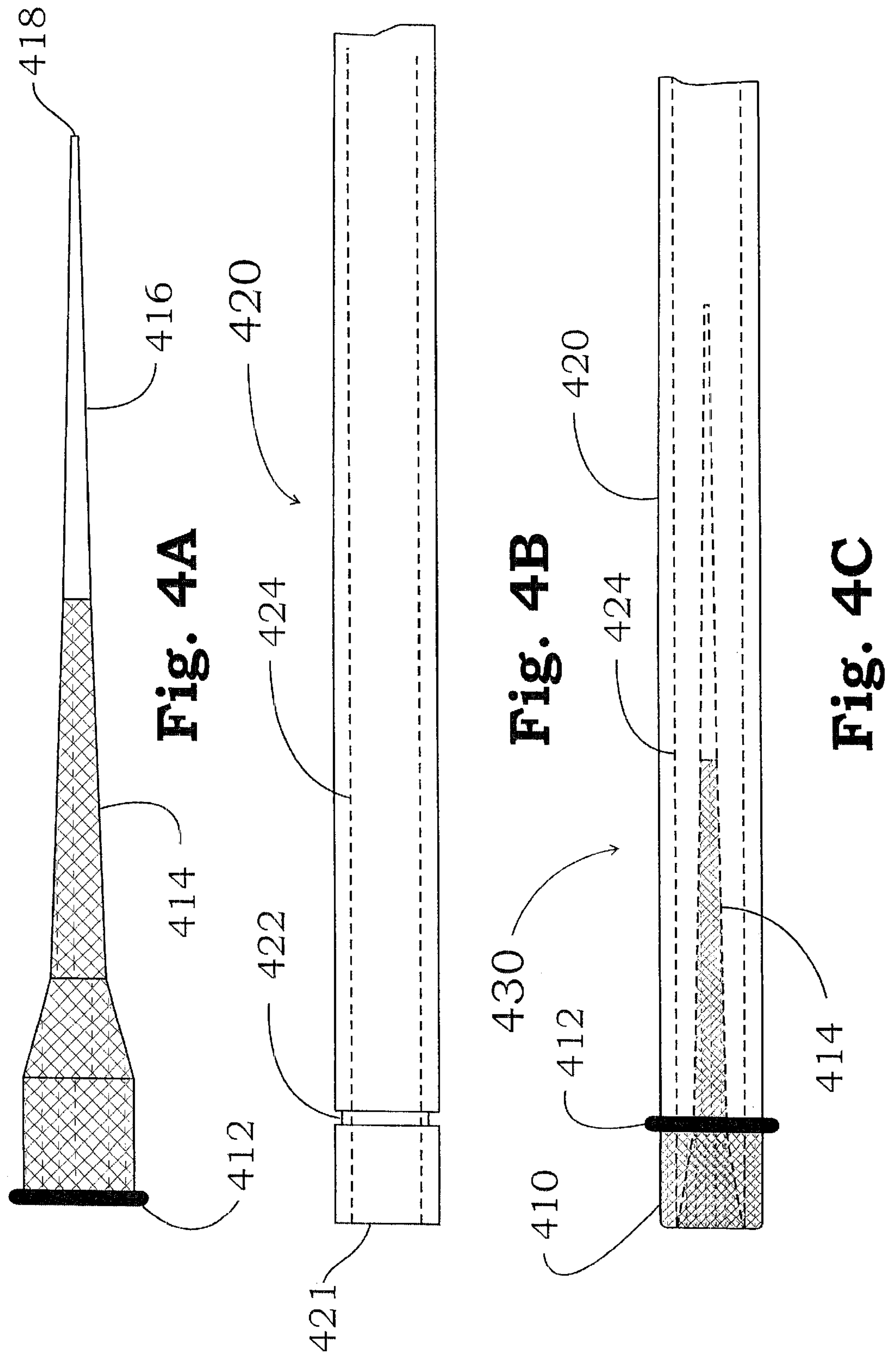
FIGS. 4A through 4F show the assembly of the embodiment of the catheter of FIGS. 3A and 3B.

FIGS. 4A, 4B and 4C show a membrane 410, a catheter tube 420, and a subassembly 430 comprising membrane 410 and tube 420. Membrane 410 can be attached to catheter tube 420 by inserting tip 418 of membrane 410 into opening 421 of tube 420, until deployable sections 414 and 416 of membrane of 410 are inside hollow 424 of tube 420. Next, a leading edge 412 of membrane 410 is snapped into a position ring 422 located on the outer surface of catheter tube 420, as shown in FIG. 4C. Positioning ring 422 can be machined or molded depending on the manufacturing process. Other chemical and/or physical means of attaching membrane 410 to tube 420 can also be used, e.g., adhesive, heat bonding, ultrasonic welding, chemical bonding or heat staking.

Figures 4D, 4E, 4F:
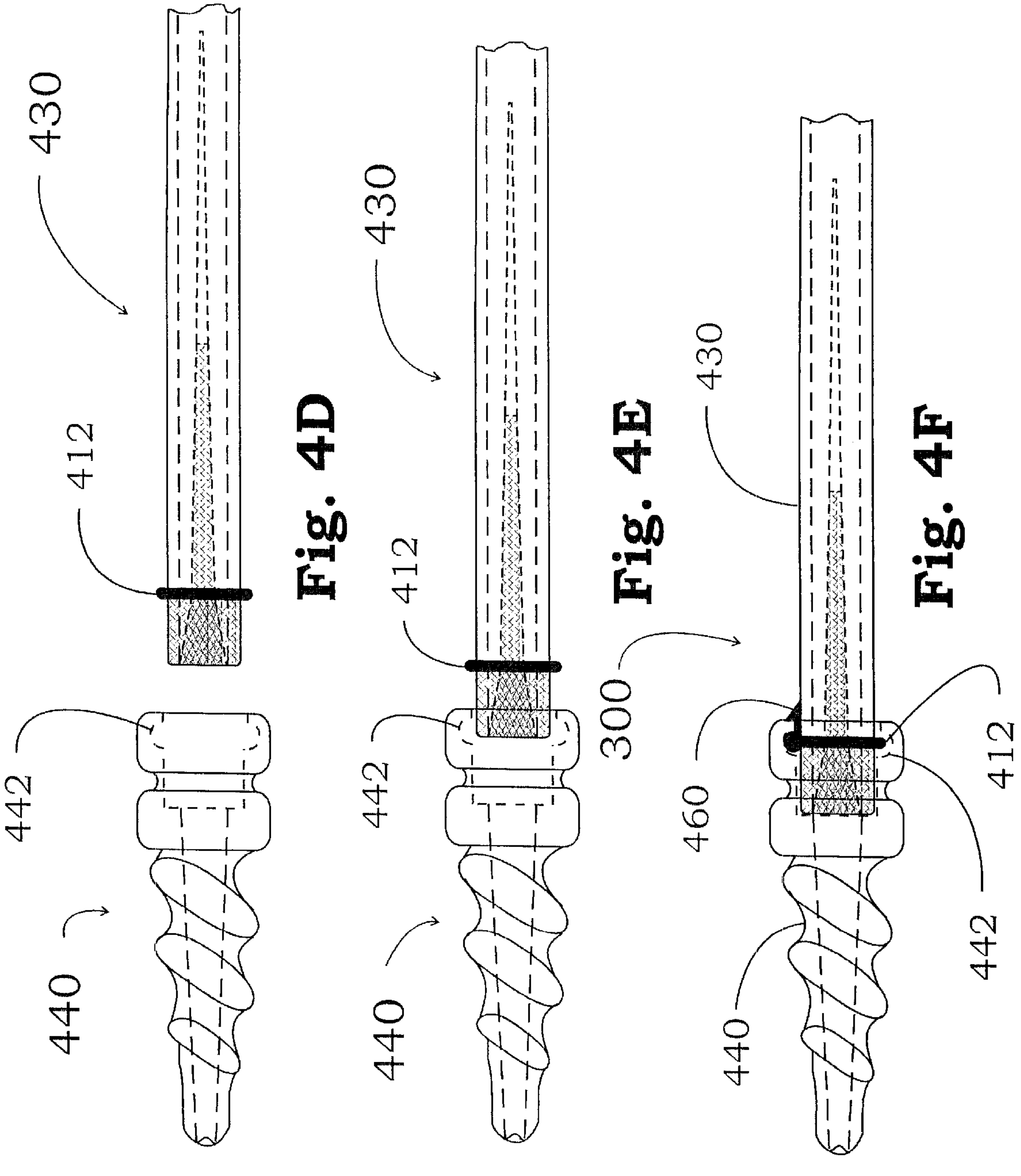

As shown in FIGS. 4D, 4E and 4F, subassembly 430 can be press fitted into catheter nozzle 440, by engaging membrane edge 412 of subassembly 430 into an internal positioning ring 442 of nozzle 440. Although subassembly 430 can be sufficiently mechanically coupled to nozzle 440, the various components of assembled catheter 300 can be further secured to each other by sonically welded or heat staked to prevent separation during deployment, such as inside the reproductive tract during artificial insemination (AI).

Alternatively, subassembly 430 can be replaced by a one-piece membrane-tube combination that can be manufactured by, for example, blow molding. Another method for constructing subassembly 430 is to insert catheter tube 420 over a membrane die, similar to dies used in balloon manufacturing, dipping the die and the attached catheter tube 420 into a suitable liquid membrane media until the entire die and about half inch of the end of catheter tube 420 is coated with the membrane media. After the liquid membrane media is cured, membrane tip 418 is cut. A downward movement of catheter tube 420 detaches tube 420 from the die and also automatically inverts membrane 410 into catheter tube 420, thereby forming subassembly 430.

Membrane tip 418 can include an opening such as a slit or a circular or oval hole. Alternatively, instead of an opening, tip 418 can include a soluble plug or a pre-weakened seal designed to dissolve or fail under pressure at the right time.

Depending on the specific application, nozzle 440 can be of different shapes and sizes, and combination thereof, including but not limited to spirals, bulbous knobs, including the nozzles illustrated by FIGS. 1A, 1B, 2A, 2B, and 2C. Although spirals are optional, approximately one to three spirals may be optimal when catheter 300 is used in swine. Shorter nozzles are also possible because membrane 410 is self-sealing, longer and self-guiding. In some embodiments, nozzle 440 is tapered to aid in insertion into the tract.

Different membrane materials and size thickness depend on applications and target animal. For virgin sows, also known as gilts, nozzle 440 may have a smaller diameter and shorter length. Conversely, for second to seventh parity sows with larger birth canals, nozzle 440 may have a larger diameter and longer length to facilitate the deposit of genetic materials and/or diagnostic instruments. For example in sows, the overall length of membrane 410 can be approximately four to eight inches and tapering gently from one-eighth of an inch.

Depending on the specific type and size of the target application, different materials, size, and thickness can be employed. Suitable materials for nozzle 440 and membrane 410 of catheter 300 include silicone, silicone gel packs, foam, latex, ClearTex™ (available from Zeller International, New York), polymers, plastics, metals, or combinations thereof. Other candidate materials include the polyolefins, polyethylene and polypropylene, the polyacetals, ploy-butadiene-styrene copolymers, the polyfluoro and polyfluorochloro-polymers, such as Teflon™ and other polymers and copolymers.

Figures 8A, 8B, 8C:
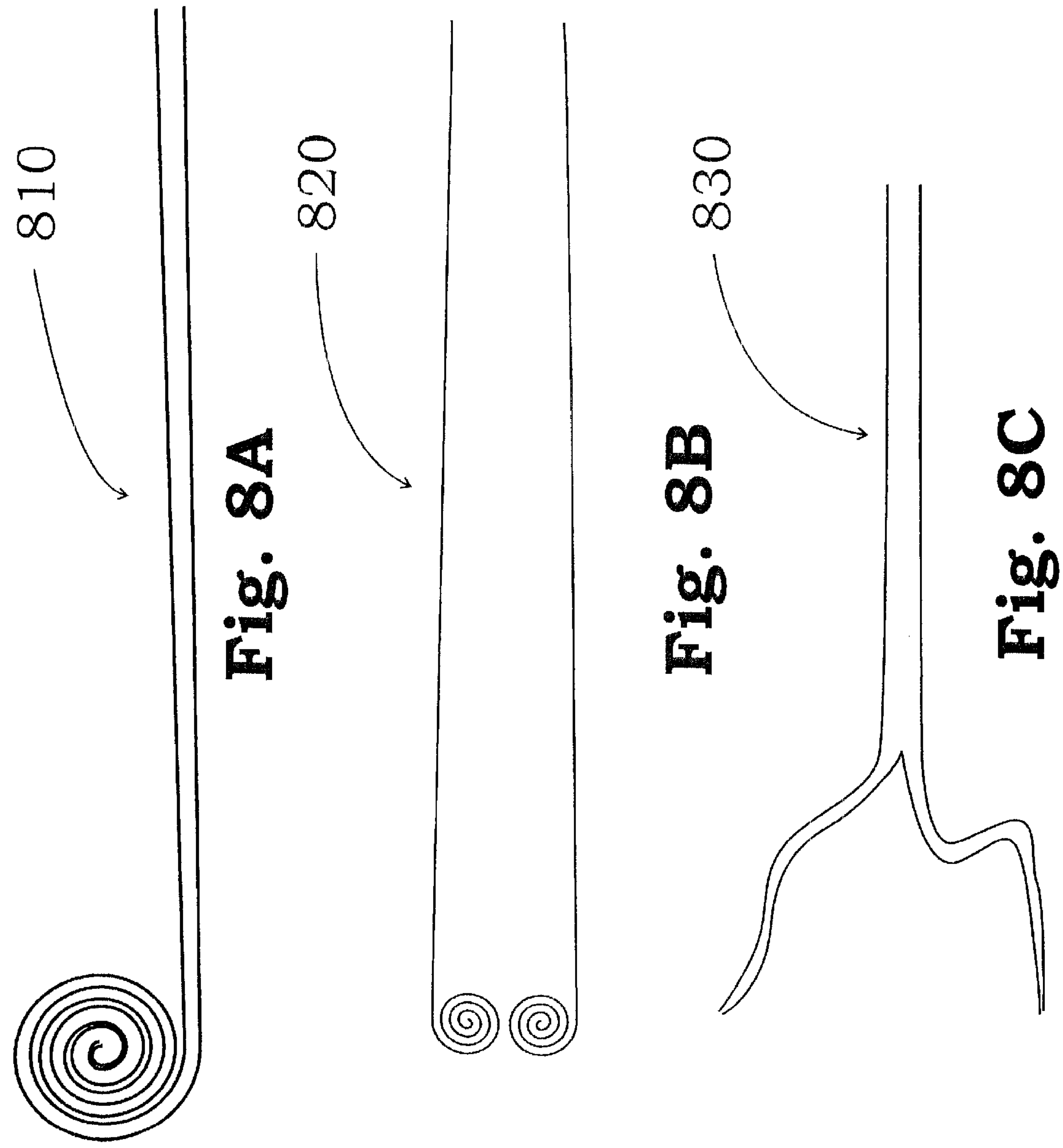
FIGS. 8A, 8B and 8C are cross-sectional views of alternative embodiments of the membrane for the catheter.

As shown in the cross-sectional views of FIGS. 8A and 8B, other embodiments include a membrane 810 that are similar to a children's party noisemaker and an inwardly-rolled embodiment 820 not unlike a condom, respectively. A twin forked-membrane 830 is also possible for deployment into the dual uterine horns of a sow, as shown in FIG. 8C.

Many variations of catheter 300 are possible. For example, catheter 300 may have multiple tubes with multiple membranes. Such an embodiment may be useful in laparoscopy where one pathway is created for a camera and a second pathway is created for an instrument during surgery. Alternatively, a large diameter catheter 300 can also be used to create a large pathway within which one or more smaller catheters can be deployed.

Figures 5A, 5B, 5C:
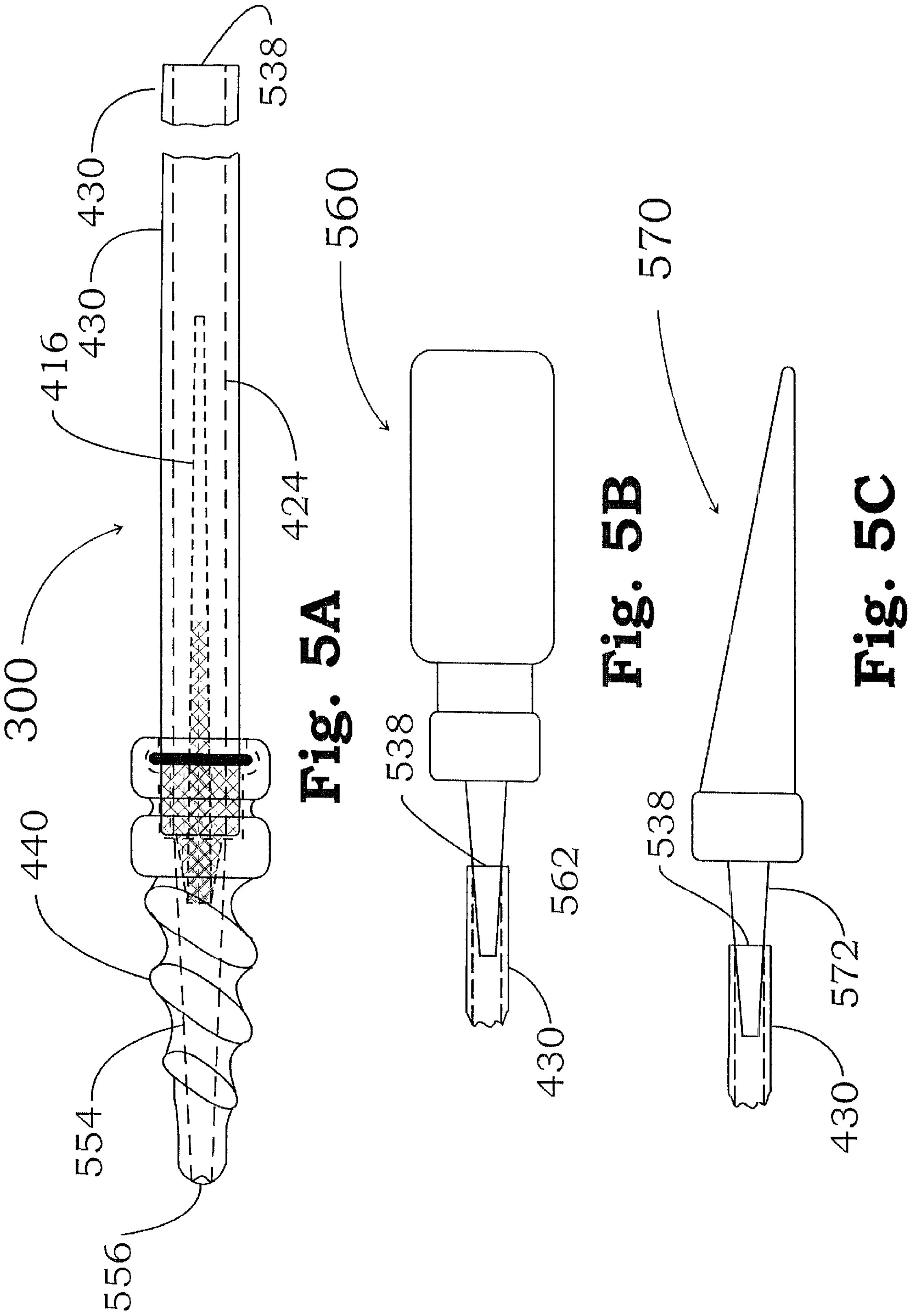
FIGS. 5A, 5B and 5C show one embodiment of the catheter attached to two exemplary AI dispensers.
Figures 5D, 5E:
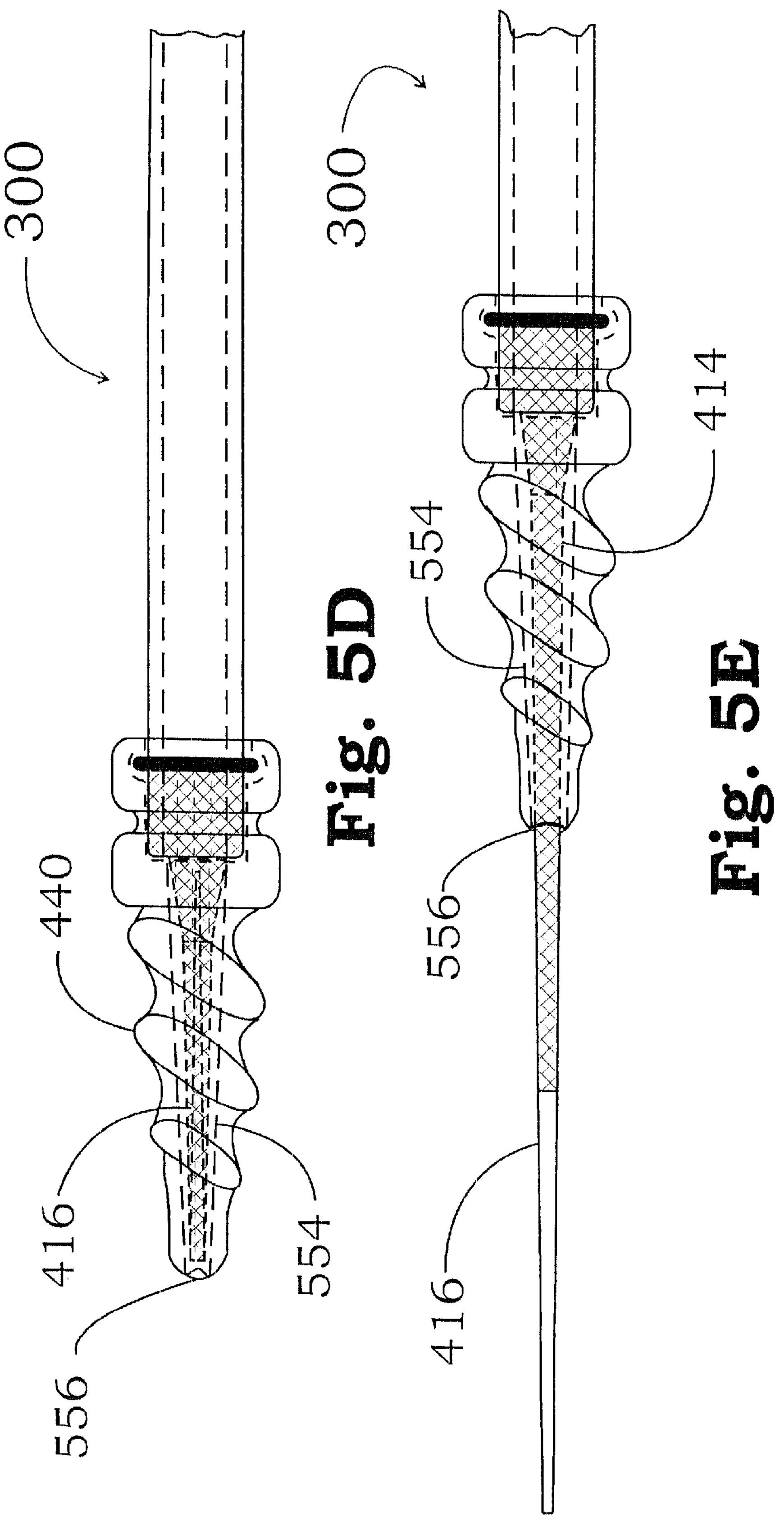
FIGS. 5D and 5E show the catheter during and after deployment.
Figure 6:
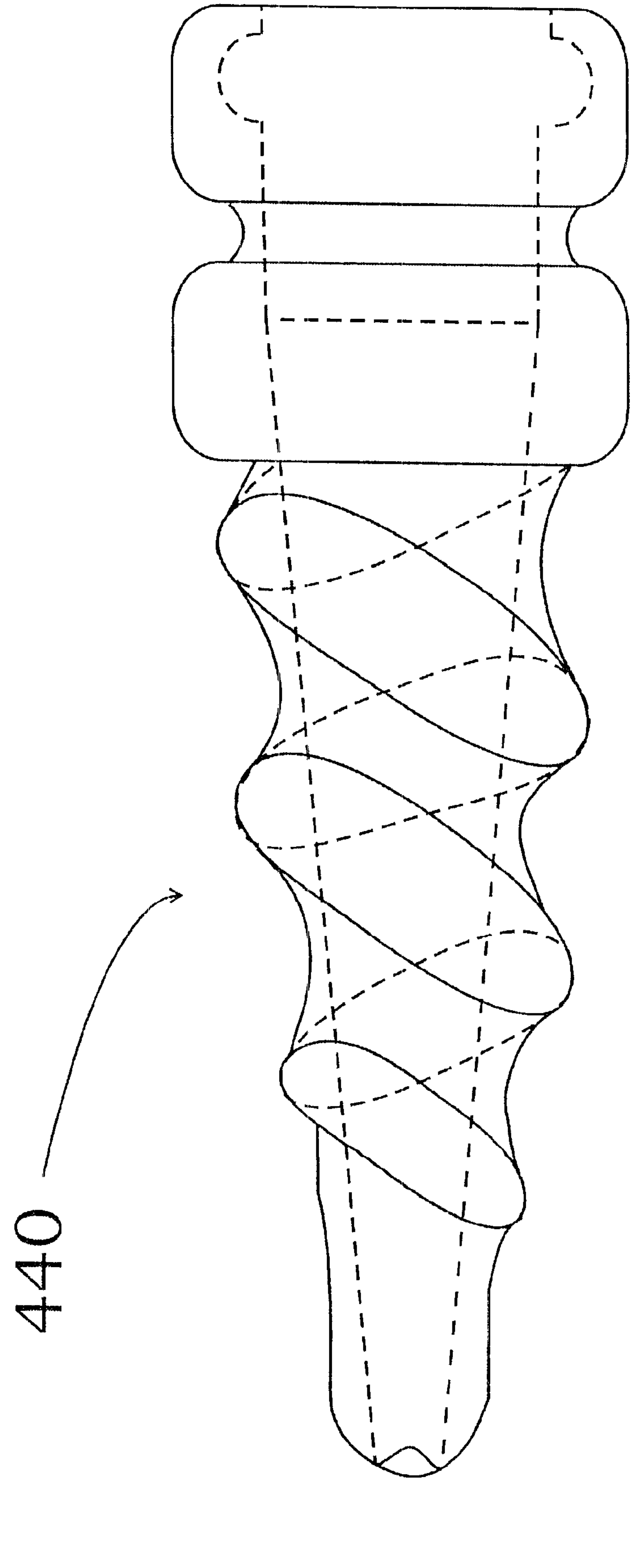
FIG. 6 is an enlarged drawing of one embodiment of a tapered nozzle for the catheter.

FIGS. 5A, 5D, and 5E, show catheter 300, before, during and after deployment, respectively. FIGS. 5B and 5C one embodiment of the catheter attached to two types of AI dispensers. FIGS. 7A through 7E show the insertion and deployment of catheter 300 in a sow 780. Catheter 300 is deployed by introducing genetic material suspended in a suitable fluid under pressure into sow 780. As shown in FIGS. 5B and 5C, the AI fluid can be transported in a suitable dispenser, such as a squeeze bottle 560 or a pre-packaged tube 570.

Figure 7A:
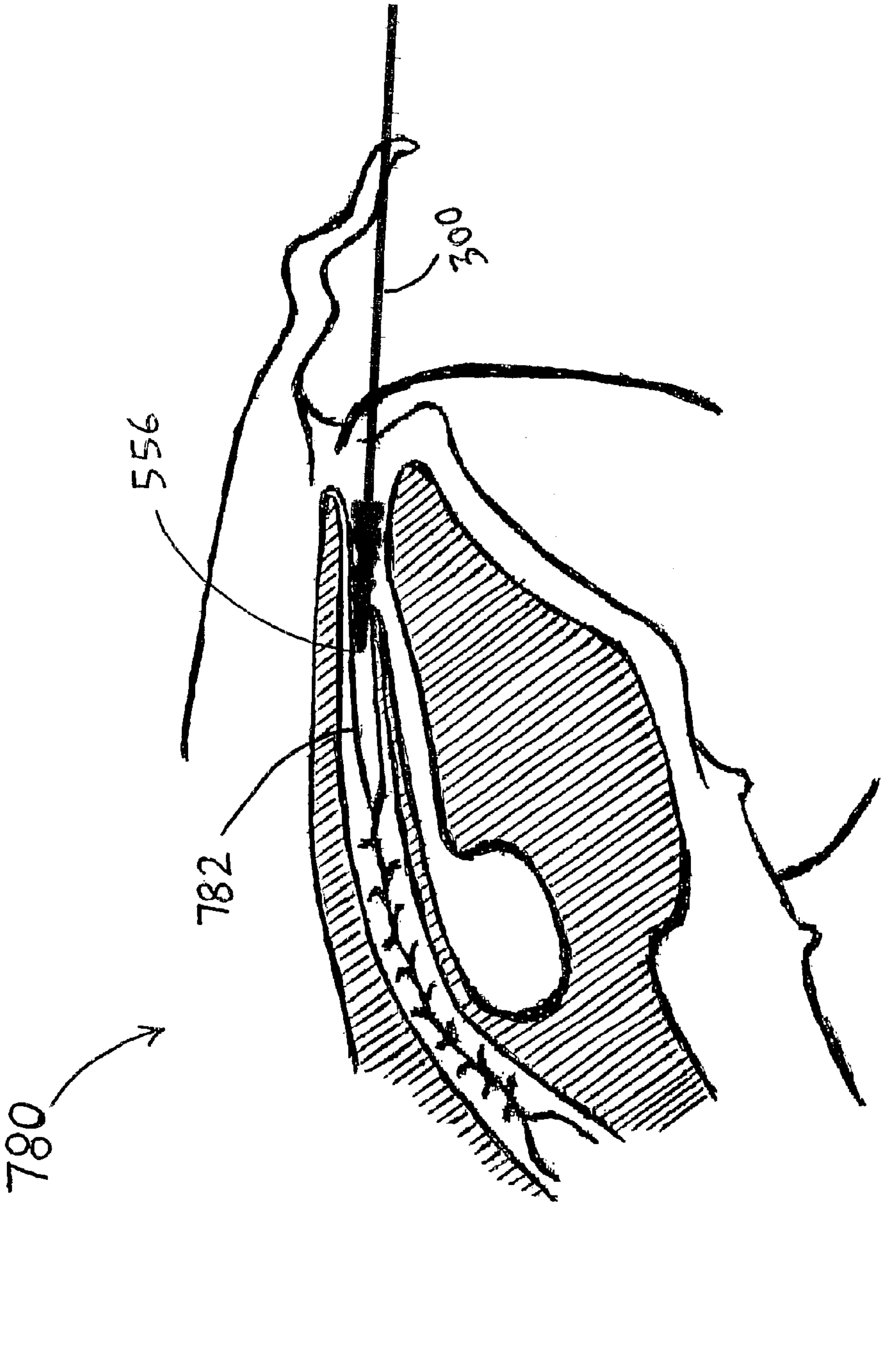
FIGS. 7A through 7E show the insertion and deployment of the catheter in a sow.
Figure 7B:
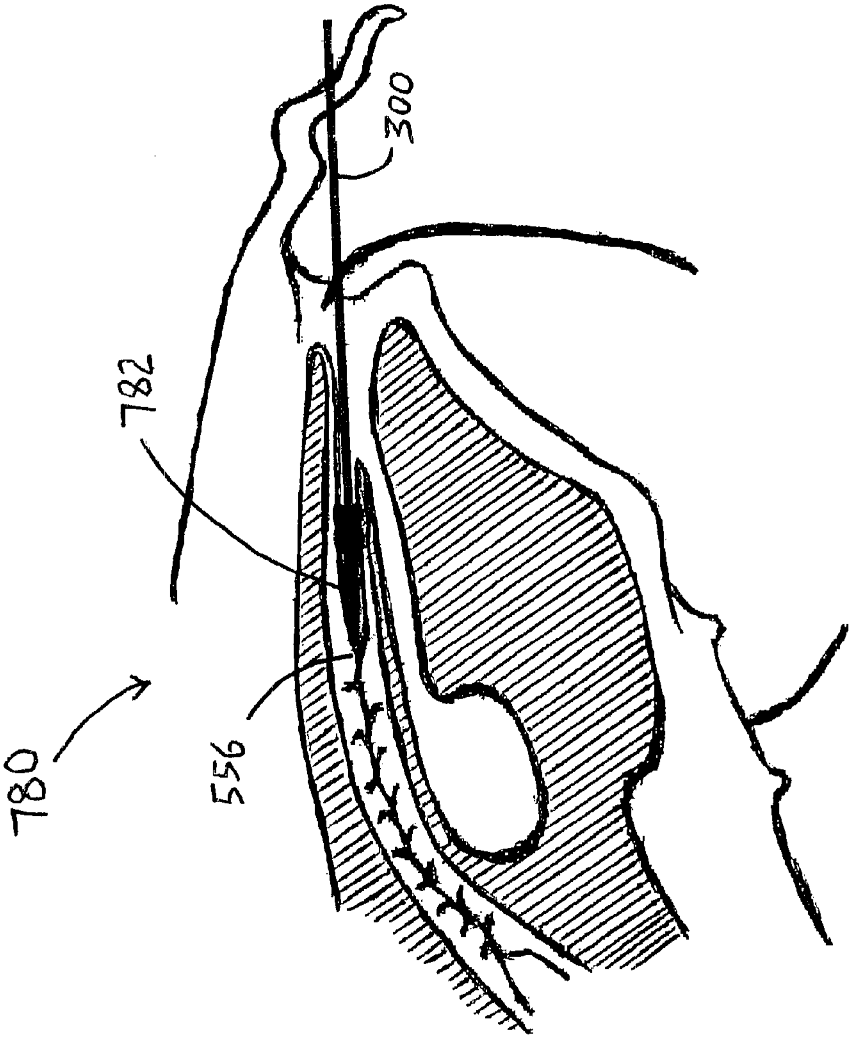

Referring to FIG. 7A, catheter 300 is inserted into vaginal cavity 782 of sow 780. Catheter 300 is gradually pushed further into sow 780 until nozzle tip 556 is fully inserted into vagina cavity 782, as shown in FIG. 7B.

Figure 7C:
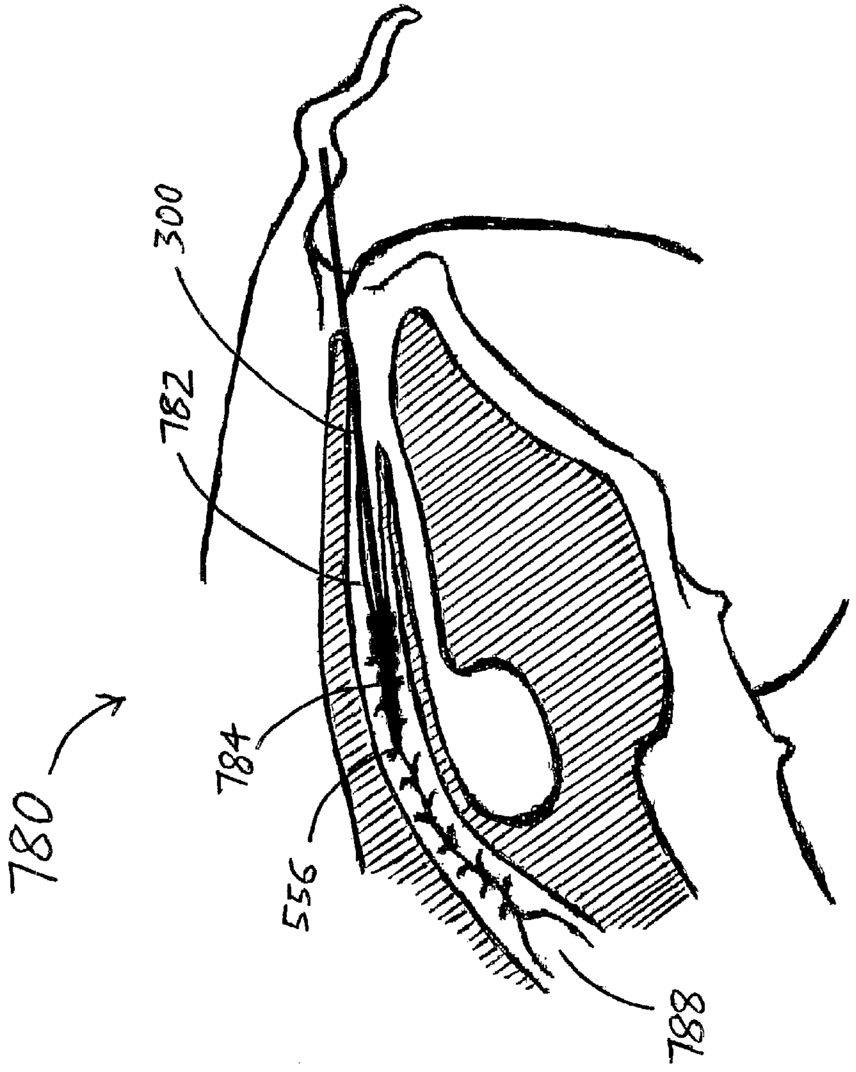

In FIG. 7C, catheter 300 is then gently eased into cervical tract 784 of sow 780 until nozzle tip 556 engages at least the first cervical ring of cervical tract 784. Unlike conventional catheters, membrane 410 is not advanced until catheter 300 is positioned in cervical tract 784, thereby preventing contaminated materials that may be contained in vaginal cavity 782, or fluids from cervical tract 784, from being accidentally transferred into uterus 788 or uterine horns of sow 780. Hence, bio-security of uterus 788 is maintained.

Figure 7D:
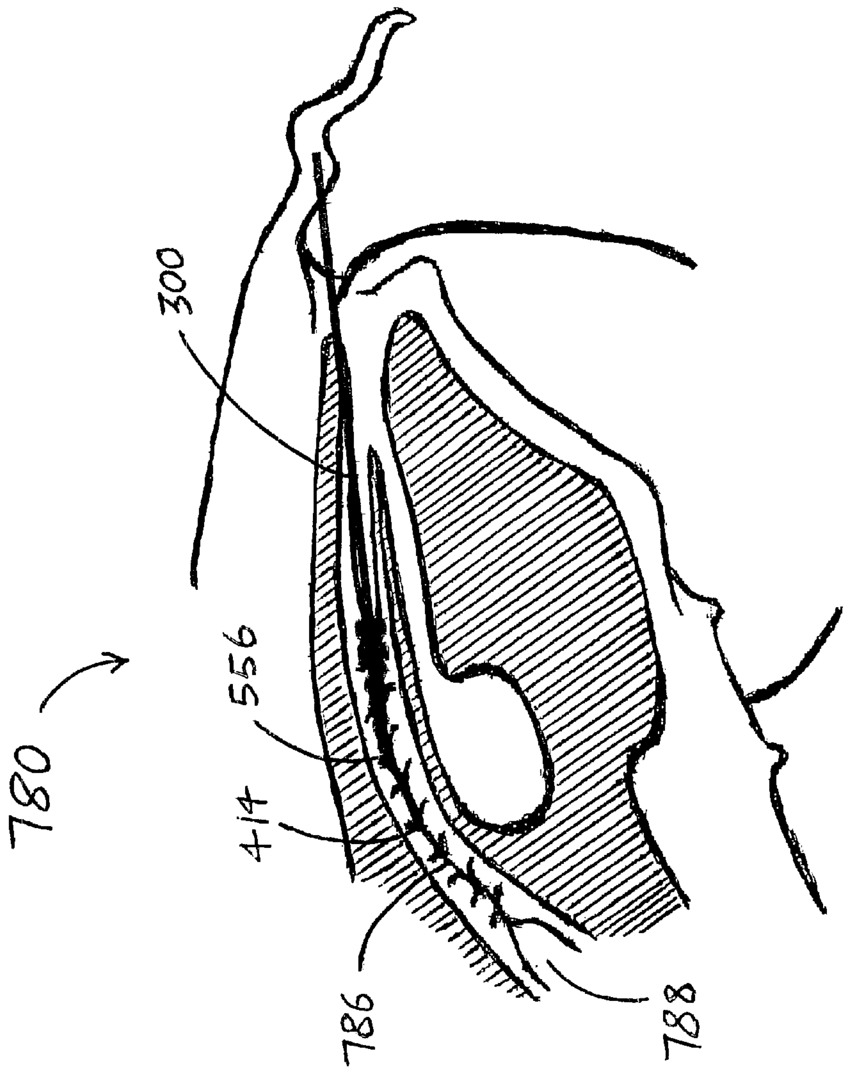

Next, as shown in FIG. 7D, AI fluid under pressure is fed into catheter 300. Pressure can be generated manually via a dispenser 560 or by a suitable pump, such as a pneumatic or hydraulic pump. The effect of the pressure causes membrane 410 to begin unfolding in an inside-out manner not unlike removing one's sock by pulling from the open end. Although catheter 300 includes an opening in membrane tip 418, the AI fluid under pressure keeps the opening of tip 418 closed until membrane 410 is fully extended into cervical tract 784.

Figure 7E:
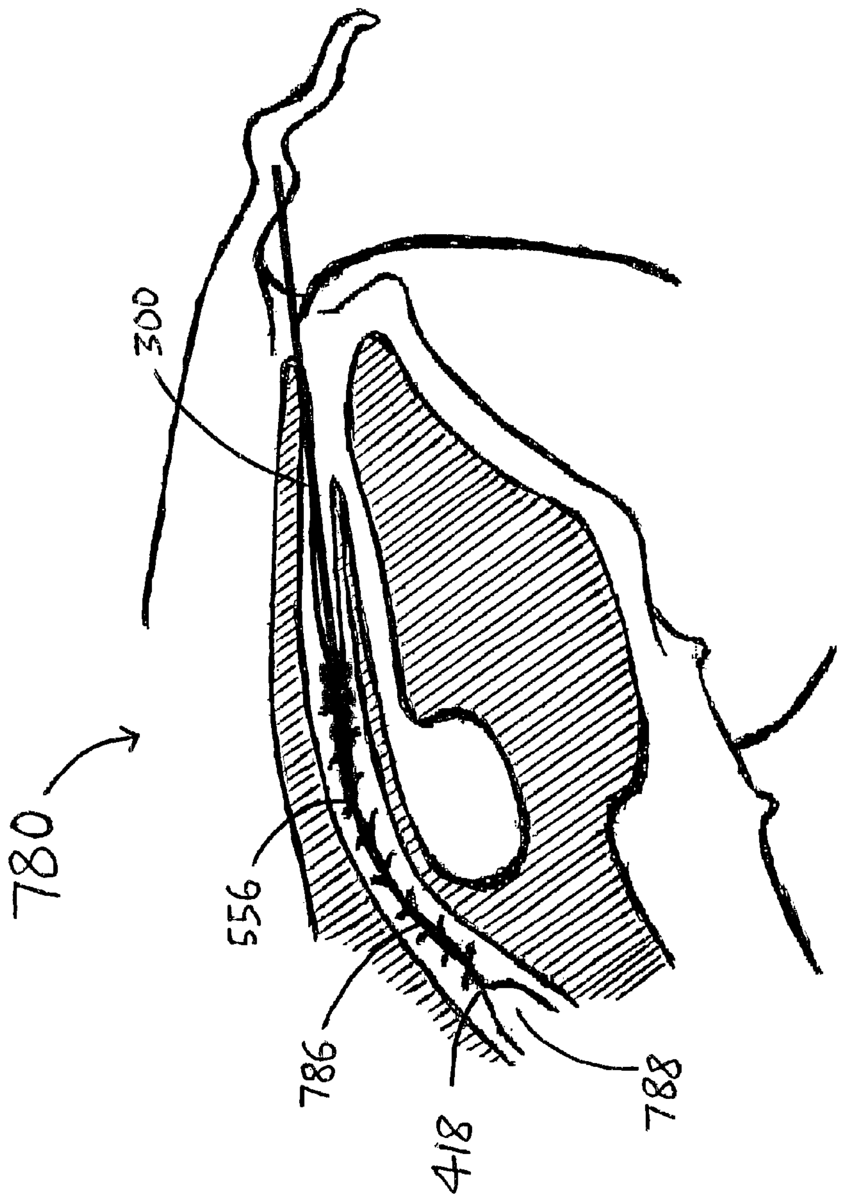

Referring now to FIG. 7E, membrane 410 of catheter 300 continues to advance in a frictionless manner into the curved and narrow passageway of cervical tract 784, automatically centering the ever-expanding forward most portion of membrane 410 in the direction of least resistance. It is this expansion and automatic centering action of membrane 410 that advantageously enables membrane 410 to worm its way through cervical tract 784 without damaging or irritating delicate tissues. Eventually, when membrane 410 is fully extended and membrane tip 418 is near to or at the entrance of uterus 788, the pressure causes tip 418 to open thereby allowing the AI fluid to be deposited at the deeper end of cervical tract 786 and/or directly into uterus 788.

While a slight taper of membrane 410 aids deployment in cervical tract 786, the taper may not be necessary for proper deployment. In some applications, partial penetration of membrane 410 into the uterine horns (not shown) is also possible, allowing for example the introduction of embryo transplants.

Hence the invention eliminates the need for multiple removable sheaths by progressively feeding new portion of membrane 410 in an unfolding process. Every newly extended portion of membrane 410 is sterile because there is no prior contact with other biological tissue, such as vaginal cavity or other body fluids.

When a suitable amount of AI fluid has been deposited into sow 780, membrane 410 collapses after the fluid pressure dissipates, allowing for safe and easy withdrawal of the relatively flat, flexible, smooth and lubricated surface of membrane 410, causing minimal discomfort and posing minimal risk of trauma and damage to the recipient animal.

The use of trans-cervical intra-uterine AI advantageously reduces the volume of AI fluid needed for successful insemination by delivering the genetic materials where nature intended, i.e., into uterus 788. For example, a normal dose of 4–6 billion fresh swine semen may be reduced to fewer than 1 billion for successful AI when trans-cervical intra-uterine AI is employed.

In conventional AI, a small window of opportunity for a successful deposit of genetic material suspended in the AI fluid occurs during standing heat, which lasts for only five to eight minutes every one to three hours during estrus, when sow 780 is receptive to boar mounting. During standing heat, when a boar mounts sow 780, cervical tract 784 clamps onto the boar's penis to assist ejaculation, and uterine contractions draws the semen through cervical tract 784. If conventional AI is attempted outside this small window of opportunity, sow 780 will not assist in the drawing of the semen through cervical tract 784, and much of the AI fluid will backflow out the sow's vulva and is wasted, thereby reducing the probability of a successful litter.

Unlike conventional AI, catheter 300 is effective during refractory heat, which is the much longer period during estrus when cervical tract 784 is relaxed, allowing easier penetration of cervical tract 784. Since catheter 300 bridges cervical tract 784 and deposits the genetic material suspended in the AI fluid much closer to uterus 788, resistance caused by clamping cervical tract 784 during standing heat is not needed and probably undesirable. Hence catheter 300 is effective during the much longer refractory heat period because semen can be deposited efficiently and with minimal restriction in cervical tract 784.

Hence the advantages of trans-cervical intra-uterine AI can be combined with the relative safety and effectiveness of catheter 300 of the present invention. Farmers can now use AI in the much longer refractory heat period, allowing these swine farms to operate more efficiently, since successful AI is no longer limited to the much shorter standing heat period.

Yet another significant advantage of the present invention is the ability of membrane 410 to deploy in a self-centering and self-directing manner, when deployed under pressure. During manufacture, a suitable lubricant may be applied to the surface of membrane 410 that may come into contact with the tract of the animal, further reducing discomfort and risk of trauma during deployment and withdrawal of catheter 300.

In addition, unlike the conventional rigid deep penetration catheters, once membrane 410 of catheter 300 has been deployed and withdrawn from cervical tract 784, it is difficult to reinsert membrane 410 back into catheter nozzle 440 and tube 420, thereby discouraging the reuse of the now contaminated membrane 410.

Once fully extended into a tract of a recipient animal, e.g., into the reproductive tract, respiratory tract, circulatory tract or digestive tract, catheter 300 provides a protective shield for the insertion of devices such as endoscopes, tracheal tubes, or other diagnostic and therapeutic instruments. Membrane 410 shields the tract from the scraping, scarring and discomfort caused by the contact and friction of the hard, semi-blunt instruments and probes on the otherwise unprotected tract. As a result, healing time and the risk of infection are significantly reduced, thereby lowering recovery time and cost.

Although the described embodiment of catheter 300 uses an inverted membrane 410 which is turned inside-out during deployment, the concepts of a self-guiding, frictionless, membrane 410 which is deployed with minimal discomfort and trauma to recipient animals has many applications. In addition to AI and embryo transplant, many other applications for catheter 300 are possible. For example, catheter 300 can also be used for diagnostic and/or therapeutic applications in which pathways are created in the reproductive tract, respiratory tract, circulatory tract or digestive tract of the recipient animal or a patient. These pathways enable procedures such as embryo transplant and drug delivery to be performed. Laparoscopic procedures such as introducing cameras and instruments are also possible. Depending on the application, the size and shape of catheter 300 may vary.

While this invention has been described in terms of several preferred embodiments, there are alterations, modifications, permutations, and substitute equivalents, which fall within the scope of this invention. It should also be noted that there are many alternative ways of implementing the methods and apparatuses of the present invention. It is therefore intended that the following appended claims be interpreted as including all such alterations, modifications, permutations, and substitute equivalents as fall within the true spirit and scope of the present invention.

What is claimed is:

1. A method of creating a pathway in a tract of an animal, useful in association with a catheter having a tube coupled to a membrane initially positioned substantially inside the tube, the method comprising:

inserting the tube into an tract of the animal; and extending the membrane from an opening in the tube and into the tract, thereby creating the pathway in the tract, and wherein the membrane is extended in the tract without sliding action between the membrane and the tract.

2. A method of creating a pathway in a tract of an animal, useful in association with a catheter having a membrane initially positioned substantially inside the catheter, the method comprising:

extending the membrane from an opening of the catheter and into the tract, thereby creating the pathway in the tract, and wherein the membrane is extended in the tract without sliding action between the membrane and the tract.

3. The method of claim 2 wherein the extension of the membrane is caused by pressure.

4. The method of claim 2 wherein the tract is the cervical tract of the animal.

5. The method of claim 4 wherein the animal is a sow.

6. The method of claim 4 further comprising depositing genetic material into the animal.

7. The method of claim 2 wherein the catheter includes a nozzle located at the opening of the catheter.

8. The method of claim 2 wherein the membrane is tapered.

9. A catheter useful for creating a pathway in a tract of an animal, the catheter comprising:

a membrane initially positioned substantially inside the catheter, the membrane configured to extend from an opening of the catheter and into the tract, and wherein the membrane extends without sliding action between the membrane and the tract.

10. The catheter of claim 9 wherein the extension of the membrane is caused by pressure.

11. The catheter of claim 9 wherein the tract is the cervical tract of the animal.

12. The catheter of claim 11 wherein the membrane is configured to deposit genetic material into the animal.

13. The catheter of claim 11 wherein the animal is a sow.

14. The catheter of claim 9 further comprising a nozzle located at the opening of the catheter.

15. The catheter of claim 9 wherein the membrane is tapered.

16. A membrane useful in association with a catheter configured to create a pathway in a tract of an animal, the membrane configured to be initially positioned substantially inside the catheter, the membrane configured to extend from an opening of the catheter and into the tract, and wherein the membrane is configured to extend without sliding action between the membrane and the tract.

17. The membrane of claim 16 wherein the extension of the membrane is caused by pressure.

18. The membrane of claim 16 wherein the tract is the cervical tract of the animal.

19. The membrane of claim 18 wherein the membrane is configured to deposit genetic material into the animal.

20. The membrane of claim 18 wherein the animal is a sow.

21. The membrane of claim 16 wherein the membrane is tapered.

22. A membrane useful in association with a catheter configured to create a pathway in a tract of an animal, the membrane configured to be initially positioned substantially inside the catheter, the membrane configured to extend from an opening of the catheter and into the tract, and wherein the membrane is configured to extend by unfolding in an inside-out manner.

23. The membrane of claim 22 wherein the extension occurs without sliding action between the membrane and the tract.

24. The membrane of claim 22 wherein the extension of the membrane is caused by pressure.

25. The membrane of claim 22 wherein the tract is the cervical tract of the animal.

26. The membrane of claim 25 wherein the animal is a sow.

27. The membrane of claim 25 wherein the membrane is configured to deposit genetic material into the animal.

28. The membrane of claim 22 wherein the membrane is tapered.

* * * * *